United States Patent [19]
Satoh

[11] Patent Number: 6,159,145
[45] Date of Patent: Dec. 12, 2000

[54] APPETITE ADJUSTING TOOL

[76] Inventor: Mieko Satoh, 1-22-4 Shimoishihara, Chofu-shi, Tokyo 182-0034, Japan

[21] Appl. No.: 09/051,041

[22] PCT Filed: Jul. 30, 1997

[86] PCT No.: PCT/JP97/02651

§ 371 Date: Mar. 31, 1998

§ 102(e) Date: Mar. 31, 1998

[87] PCT Pub. No.: WO98/05381

PCT Pub. Date: Feb. 12, 1998

[30]     Foreign Application Priority Data

Aug. 2, 1996  [JP]  Japan ..................................... 8-204604
Jul. 1, 1997  [JP]  Japan ..................................... 9-188930

[51] Int. Cl.[7] ............................................... A61M 37/00
[52] U.S. Cl. ............................................................ 600/12
[58] Field of Search ..................... 600/9–12; 128/897–99

[56]              References Cited

FOREIGN PATENT DOCUMENTS 1-270875  10/1989  Japan .
5-317354  12/1993  Japan .

OTHER PUBLICATIONS

Microfilm of the specification and drawings annexed to the written application of Japanese Utility Model Application No. 30738/1978 (Laid–Open No. 133994/1979) (Tomio Sudo), Sep. 17, 1979.

*Primary Examiner*—John P. Lacyk
*Attorney, Agent, or Firm*—McDermott, Will & Emery

[57]              ABSTRACT

An appetite adjusting tool is composed of a piece having, at its front end, a stimulus giving section with a cross section that can be inserted into the external auditory canal of the ear of a person, for providing a magnetic stimulus to nerves which give an influence to the sense of taste and appetite from a predetermined position of an internal wall of the external auditory canal. A magnetism generated from the stimulus giving section stimulates the vagus nerve and the glossopharyngeal nerve, to restrict an appetite and to make a person sense a sweet taste as a bitter taste, to thereby achieve an effective dieting.

18 Claims, 5 Drawing Sheets

APPETITE ADJUSTING TOOL

FIELD OF THE INVENTION

The present invention relates to an appetite adjusting tool capable of restricting an appetite of a person by changing the person's sense of taste when the tool is inserted into an ear.

BACKGROUND OF THE INVENTION

In recent years, people are becoming more concerned about dieting as they tend to have increasing interest in more healthy life. Overweight persons challenge diet for preventing adult diseases such as high blood pressure and diabetes, especially, females tend to enter on various forms of diet for maintaining their health and shapes.

Conventional methods of diet have basically been focused on how to reduce the volume of a meal or how to reduce caloric intake. However, in general, it is difficult to make persons establish a habit of taking low-calorie food for a long period of time, and some persons will abandon their efforts in the middle.

SUMMARY OF THE INVENTION

It is an object of the present invention to provide an appetite adjusting tool for making a person restrict the intake of sweets having high calorific values by making the person sense a sweet taste of a food as a bitter taste when the tool is inserted into the external auditory canal of the ear of the person.

In order to achieve the above-described object, an appetite adjusting tool according to the present invention includes a stimulus giving section which has a cross section that can be inserted into the external auditory canal of the ear of a person, and provides a magnetic stimulus to nerves which give an influence to the sense of taste and appetite from a predetermined position of an internal wall of the external auditory canal.

The rear end of the stimulus giving section in the direction of insertion of the appetite adjusting tool into the external auditory canal may be connected to a bar member of a predetermined length extending along the direction of insertion. Alternatively, the appetite adjusting tool may be composed of only the stimulus giving section without the bar member.

Preferably, the stimulus giving section is composed of a non-magnetic hollow unit and a magnet fixedly arranged within this hollow unit. The magnet has a shape extending long in the direction of insertion into the external auditory canal, and any one side of the magnet may be an N pole or an S pole.

DETAILED DESCRIPTION OF THE PREFERRED EMBODIMENTS

A first embodiment of the appetite adjusting tool according to the present invention will be explained below with reference to FIGS. 1 to 6C.

Figure 1:
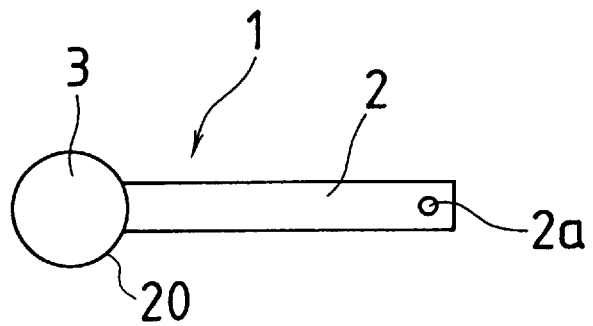
FIG. 1 is a front view of an appetite adjusting tool according to one embodiment of the present invention.
Figure 2:
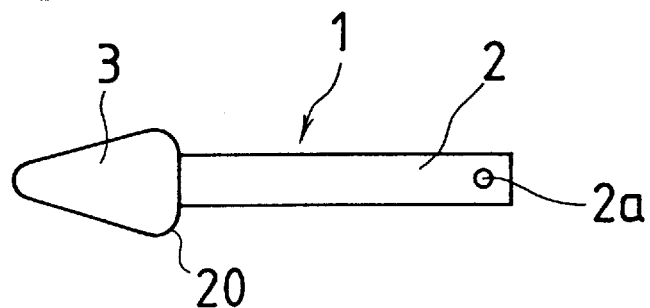
FIG. 2 is a front view of an appetite adjusting tool according to a first modification of one embodiment of the present invention.
Figure 3:
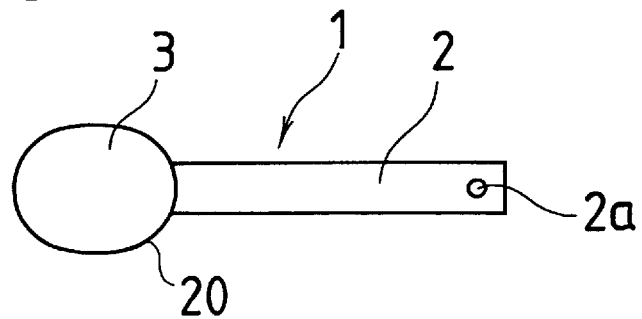
FIG. 3 is a front view of an appetite adjusting tool according to a second modification of one embodiment of the present invention.

As shown in FIGS. 1 to 3, an appetite adjusting tool 1 includes a bar section 2 having a length sufficient to be inserted into the external auditory canal of a person and a stimulus giving section 3 provided at one end of the bar section 2. The appetite adjusting tool 1 may be inserted either into one ear of person or into both ears by preparing two appetite adjusting tools 1.

The length of the bar section 2 is set such that when one end of the bar section is inserted into the external auditory canal, the other end protrudes outside from the ear. In general, it is desirable that the bar section 2 has a length of about 30 mm, but may be adjusted to be either longer or shorter depending on the situation. The bar section 2 has a circular cross section, with a diameter of about 5 mm. However, the cross section of the bar section 2 is not limited to a circular section, but may have any other sections such as oval, square rectangular, a polygonal shape or any other shapes.

A material for making up the bar section 2 is selected from among a metal such as aluminum or the like, a porcelain, a synthetic resin such as a plastic, etc. The surface of the bar section 2 may have a decoration effect by being suitably colored in silver, gold, white, blue, green, pink, orange, or others. When the bar section 2 is to be formed by a metal material, the bar section may be given an image of quality article by being plated with precious metals such as gold or platinum. Alternatively, when the bar section 2 is formed from a crystal, glass or a transparent plastic material, the bar section 2 can be made to look fine by the effect of irregular reflection of beams such as sunbeam.

Further, a small hole 2a for piercing a chain or the like through it may be provided at the rear end of the bar section 2 (the end portion opposite to the end portion where the stimulus giving section 3 is provided). When a chain (not shown) of a predetermined length is pierced through this hole 2a and put around a neck, the appetite adjusting tool can be made to look like a pendant.

At the front end of the bar section 2, a hollow unit 20 which constitutes a stimulus giving section 3 is formed integral with the bar section 2 or is fitted to the bar section with screws. A magnet 4, to be described later in detail, is fit within the hollow unit 20. In other words, both the hollow unit 20 and the magnet 4 constitute the stimulus giving section 3.

The hollow unit 20 constituting the stimulus giving section 3 is formed from a non-magnetic material such as a crystal, a metal, a porcelain or a synthetic resin like a plastic. It is desirable from the viewpoint of design that the hollow unit 20 and the bar section 2 are made from the material and in the same color. When the hollow unit 20 is made of cotton and the magnet 4 is put inside this hollow unit, the appetite adjusting tool 1 looks like an applicator.

The hollow unit 20 may have various shapes such as a sphere (FIG. 1), a cone (FIG. 2), a spheroid (FIG. 3), etc. In integrally forming the hollow unit 20 with the front end of the bar section 2 or installing the hollow section 20 on the front end of the bar section 2, the center of the hollow unit 20 (in the case of a sphere) needs to coincide with the axis of the bar section 2 or the axis of the bar section 2 and the axial center of the hollow section 20 coincide with each other (in the case of a cone, a spheroid, etc.).

When the hollow unit 20 has a spherical shape as shown in FIG. 1, the diameter of the sphere is set so that the hollow unit 20 is allowed to pass through the external auditory canal of a user while keeping contact with the inner wall of the external auditory canal. More particularly, the diameter of the sphere is between about 5 mm and 15 mm. The thickness of the wall forming the hollow unit 20 is about 1.2 mm.

When the hollow unit 20 has a shape of a cone or a spheroid other than a spherical shape, the size (diameter) of a cross section (circle) in a direction perpendicular to the center axis is set so that the hollow unit 20 is allowed to pass through the external auditory canal of a person while keeping contact with the inner wall of the external auditory canal. More particularly, a maximum value of the diameter of the circular cross section needs to be between about 5 mm and 15 mm, similar to the case of the sphere. The length of the hollow unit 20 in its axial direction is about 15 mm.

The hollow unit 20 of the stimulus giving section 3 may have, in its wall, a plurality of small through holes (not shown) allowing magnetic lines of force to pass through from the magnet 4 placed within the hollow unit to the outside.

The internal structure of the stimulus giving section 3 in the appetite adjusting tool according to a first embodiment of the present invention will be explained below with reference to FIGS. 4 to 6C.

Figure 4:
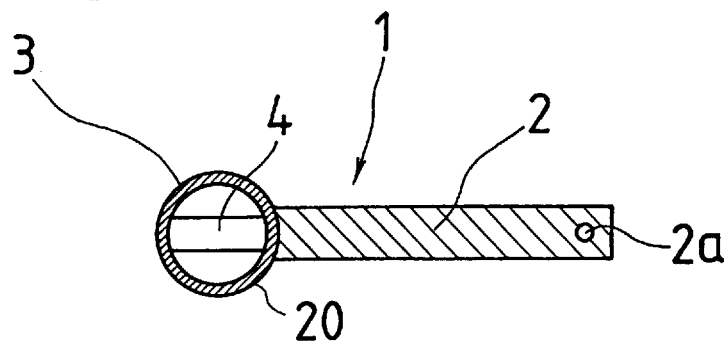
FIG. 4 is a cross sectional view of the appetite adjusting tool shown in FIG. 1.
Figure 5A:
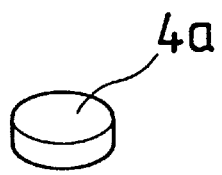
FIG. 5A is a perspective view of one element for structuring a magnet to be used in the appetite adjusting tool shown in FIG. 4.
Figure 5B:
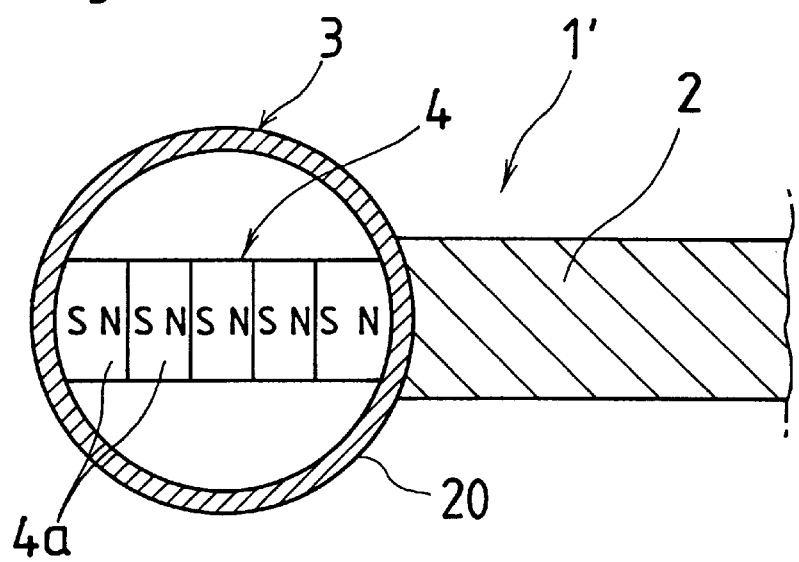
FIG. 5B is an enlarged view of a principal portion showing that the magnet in the appetite adjusting tool shown in FIG. 4 is made up by accumulating a plurality of magnets shown in FIG. 5A.
Figure 5C:
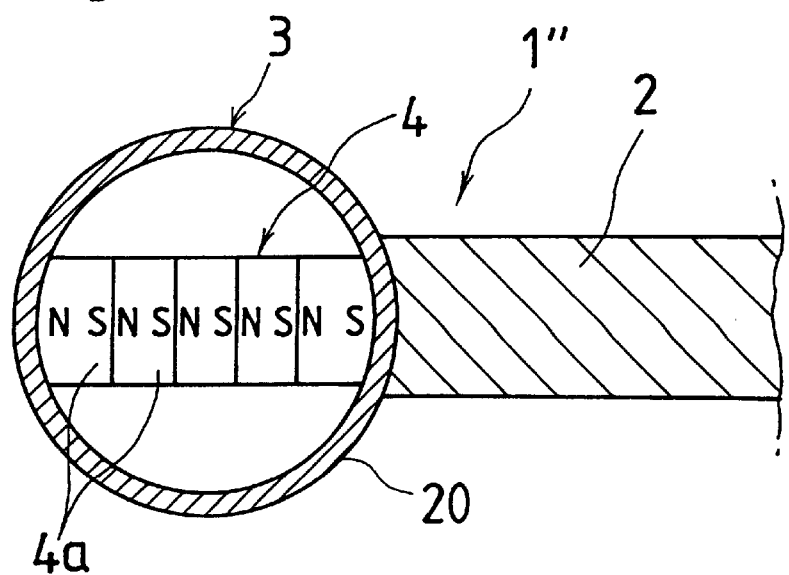
FIG. 5C is an enlarged view of a principal portion showing that the positions of the N pole and the S pole in the appetite adjusting tool may be opposite to those shown in FIG. 5B.

The hollow unit 20 of the stimulus giving section 3 has a spherical shape. Inside the hollow unit 20, a bar-shaped magnet 4 having a predetermined length is fixed with its axis coinciding with the axis of the bar section 2, as shown in FIG. 4. The bar-shaped magnet 4 is formed by laminating a plurality of disk-shaped magnets 4a as shown in FIG. 5A, for example, by laminating five pieces magnets as shown in FIG. 5B and FIG. 5C. The bar-shaped magnet 4 may have the N pole and S pole at any side. According to the example shown in FIG. 5B, the magnet 4 formed in a bar shape by being laminated as described above has the N pole at the end portion on the side of the bar section 2 and the S pole at the end portion farthest from the bar section 2. On the other hand, according to the example shown in FIG. 5C, the magnet 4 formed in a bar shape has the S pole at the end portion nearest to the bar section 2 and the N pole at the end portion farthest from the bar section 2.

Figure 6A:
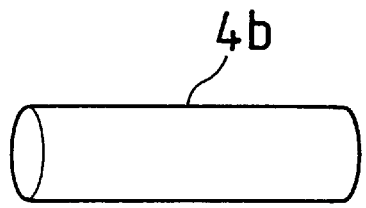
FIG. 6A is an enlarged view of a principal portion showing that the magnet in the appetite adjusting tool shown in FIG. 4 is composed of a single magnet unlike the cases of FIG. 5B and FIG. 5C.

Further, the magnet 4 may be a single magnet 4b formed bar-shaped as shown in FIG. 6A. In this case too, this magnet 4b, fit in the hollow unit 20 of the stimulus giving section 3, may have its N pole arranged on the side closer to the bar section 2 as shown in FIG. 6B or the S pole arranged on the side closer to the bar section 2 as shown in FIG. 6C.

The magnetic force of the magnet 4 is set at a value from 1,000 to about 2,000 gausses, desirably for about 1,800 gausses.

Figure 6B:
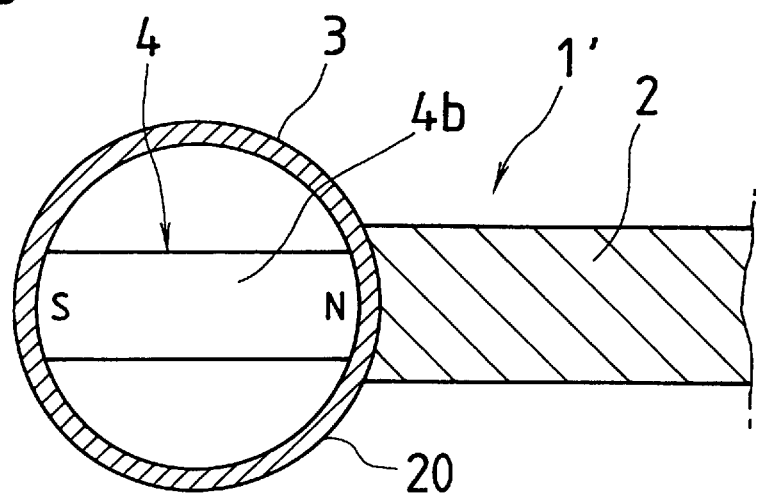
FIG. 6B is an enlarged view of a principal portion showing that the magnet in the appetite adjusting tool shown in FIG. 4 is composed of the magnet shown in FIG. 6A.
Figure 6C:
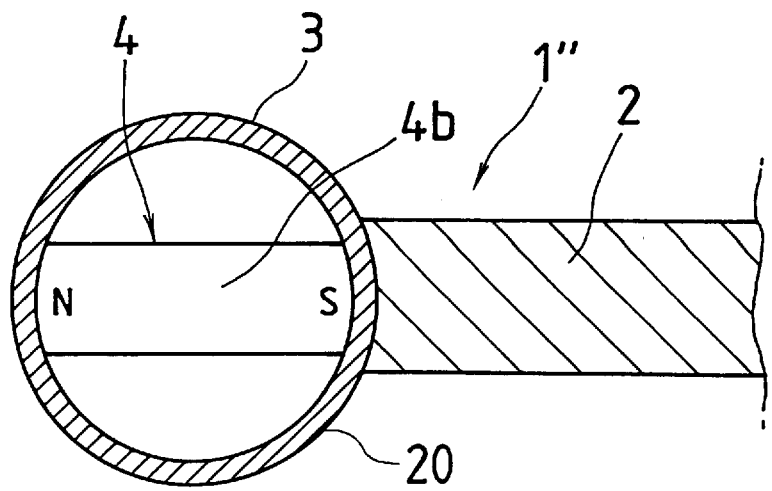
FIG. 6C is an enlarged view of a principal portion showing that the position of the N pole and S pole in the appetite adjusting tool may be opposite those shown in FIG. 6B.

When two appetite adjusting tools 1 are to be used for both ears, it is to be so arranged that one of the appetite adjusting tools 1 has the N pole of the magnet 4 arranged on the side closer to the bar section 2 as shown in FIG. 5B and FIG. 6B while the other appetite adjusting tool 1 has the S pole of the magnet 4 arranged on the side closer to the bar section 2 as shown in FIG. 5C and FIG. 6C.

The method of using the appetite adjusting tool 1 will be explained next.

To use the appetite adjusting tool 1, the bar section 2 is held between fingers and the stimulus giving section 3 is inserted into an external auditory canal 9 from an auricle 8 of an ear. In this case, if the hollow unit 20 of the stimulus giving section 3 has a spherical shape as shown in FIG. 1, it can be inserted easily into the external auditory canal 9 with a satisfactory feeling of mounting.

Figure 10:
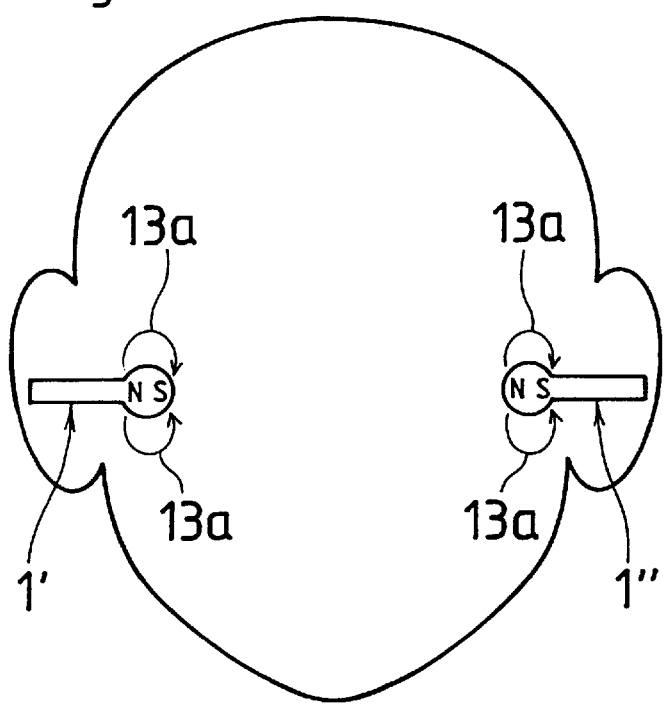
FIG. 10 is a diagram showing a desirable arrangement of the N pole and the S pole of the appetite adjusting tool of FIG. 1, where two sets, one for left ear and the other for right ear, are used for one person.

When the appetite adjusting tools 1 are to be used for both ears, the appetite adjusting tool 1 having the N pole of the magnet 4 disposed on the side closer to the bar section 2 (shown by a reference number 1' in FIG. 10) is used for the right ear, and the appetite adjusting tool 1 having the S pole of the magnet 4 disposed on the side closer to the bar section 2 (shown by a reference number 1" in FIG. 10) is used for the left ear. The reason for using the appetite adjusting tools 1 whose magnetic poles of the magnets 4 are reversed to each other for the left ear and the right ear is based on the idea of "Qui-Gong", a traditional Chinese health care method, in which a human body is considered to have S pole on its right side and N pole on its left side, and thus the magnetic poles of each appetite adjusting tools 1 are disposed so as not to break this balance.

Figure 9:
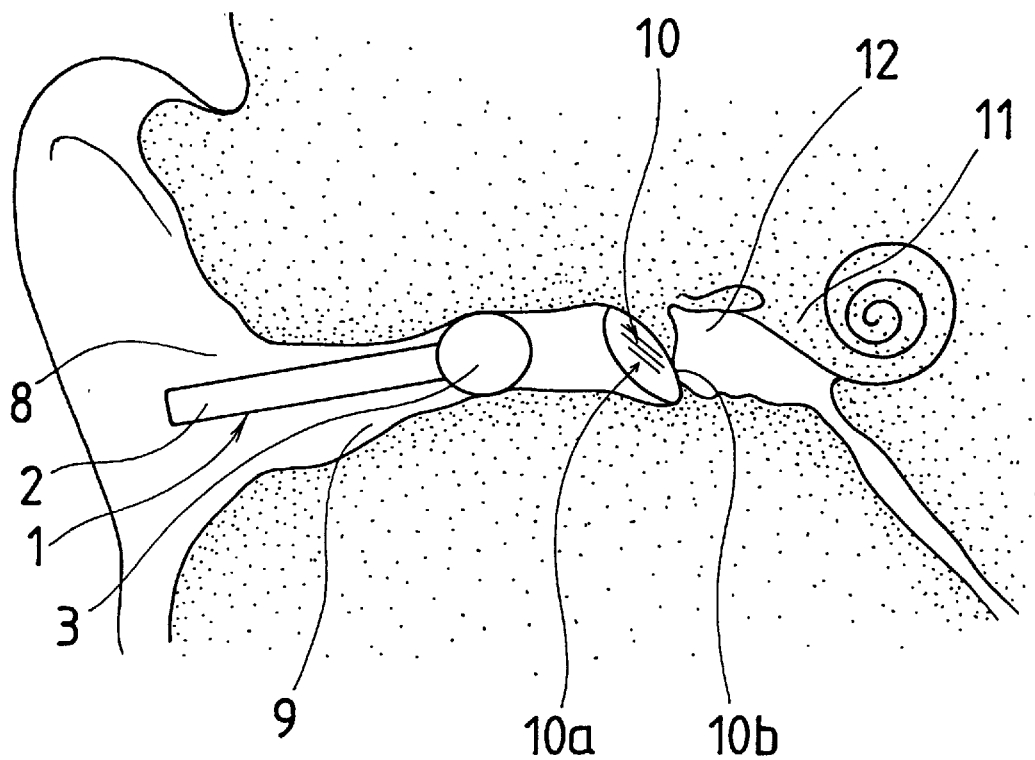
FIG. 9 is a diagram for explaining an effect of an appetite adjusting function on a person when the appetite adjusting tool shown in FIG. 1 is inserted into the external auditory canal thereof.

The ear has a structure as shown in FIG. 9. The external auditory canal 9 has a length of about 4 to 5 cm, and a drum membrane 10 exists at its front end. An internal ear 11 exists inside the drum membrane 10. A space section between the drum membrane 10 and the internal ear 11 is a middle ear 12. At the outside of the drum membrane 10, a vagus nerve 10a and others exist, and a glossopharyngeal nerve 10b exists inside the drum membrane 10.

Magnetic lines of force 13a (FIG. 10) are generated from the stimulus giving section 3 of the appetite adjusting tool 1 inserted into the external auditory canal 9 of both ears respectively, and a magnetism according to these magnetic lines of force gives a stimulus to at least the vagus nerve 10a and the glossopharyngeal nerve 10b which exist in the drum membrane 10.

Exciting the vagus nerve 10a brings about a vomiting effect through a vagus nerve image visceral motor branch.

This vomiting effect, if at a suitable level, acts to restrict user's appetite. Further, giving stimulus to the glossopharyngeal nerve 10b would result in generation of bitter saliva due to the transmission of visceral maneuverability to the low saliva nucleus and the transmission of a specific sense of taste to the tongue, thereby making a person sense bitter when a sweet taste is to be sensed by nature, with the result that the stimulus to the glossopharyngeal nerve 10b acts to restrict the appetite of sweet foods.

The above was verified by a sense of taste test by using the appetite adjusting tool according to the present invention. This sense of taste test was carried out for 29 Japanese women, as subjects, who attend a cooking school in Tokyo, Japan.

The appetite adjusting tool 1 used for this test was the appetite adjusting tool 1' as shown in FIG. 5B. The hollow unit 20 of the stimulus giving section 3 was of a spherical shape having a diameter of 10 mm made of an aluminum alloy plated with gold, and the magnetic force of the magnet 4 was 1,500 gausses in total. Further, the bar section 2 was also of an aluminum alloy plated with gold.

As a method of this test, at first, (1) a sugar (a granulated sugar) is held in a mouth, and a sense of sweet taste confirmed is given 10 while a sense of bitter taste confirmed is given 0 and these values are used as reference values in the sense of taste test to be carried out thereafter. Next, (2) the appetite adjusting tool 1 was inserted deep into the right ear and was taken out in 5 minutes, and the sugar was held in the mouth of each subject, and sensed sweetness and sensed bitterness were expressed in numerical values ranging from 0 to 10. Then, (3) after 20 minutes, the appetite adjusting tool 1 was inserted deep into the left ear and was taken out in 5 minutes, and the sugar was held in the mouth and sensed sweetness and sensed bitterness were determined in numerical values ranging from 0 to 10.

The results of the test of sense of taste are shown in the following table.

| | RIGHT EAR | | LEFT EAR | |
|---|---|---|---|---|
| AGE | SENSED SWEETNESS | SENSED BITTERNESS | SENSED SWEETNESS | SENSED BITTERNESS |
| 29 | 4 | 0 | 5 | 5 |
| 27 | 5 | 0 | 4 | 6 |
| 26 | 5 | 0 | 2 | 8 |
| 29 | 7 | 0 | 6 | 4 |
| 28 | 5 | 0 | 3 | 7 |
| 26 | 6 | 0 | 3 | 7 |
| 26 | 4 | 0 | 2 | 8 |
| 31 | 5 | 0 | 3 | 7 |
| 27 | 6 | 0 | 1 | 9 |
| 24 | 6 | 0 | 2 | 8 |
| 25 | 4 | 0 | 4 | 6 |
| 23 | 4 | 0 | 4 | 6 |
| 22 | 5 | 0 | 4 | 6 |
| 25 | 4 | 0 | 3 | 7 |
| 28 | 7 | 0 | 0 | 10 |
| 24 | 7 | 0 | 0 | 10 |
| 29 | 5 | 0 | 3 | 7 |
| 30 | 4 | 0 | 3 | 7 |
| 29 | 4 | 0 | 2 | 8 |
| 27 | 5 | 0 | 3 | 7 |
| 26 | 4 | 0 | 1 | 9 |
| 25 | 4 | 0 | 2 | 8 |
| 26 | 7 | 0 | 4 | 6 |
| 25 | 4 | 0 | 2 | 8 |
| 31 | 2 | 0 | 4 | 6 |
| 26 | 5 | 0 | 3 | 6 |
| 29 | 1 | 0 | 3 | 7 |
| 21 | 4 | 0 | 0 | 10 |
| 19 | 6 | 0 | 0 | 10 |

From the above results, it has been known that when the appetite adjusting tool 1 is inserted into the left ear, a sweet taste is sensed as a bitter taste. It is assumed that this is because nerves which have an influence on the sense of taste are concentrated near the inner wall of the external auditory canal of the left ear.

Therefore, it is possible to achieve a sufficient dieting effect by inserting the appetite adjusting tool 1 into only the left ear, instead of inserting the appetite adjusting tools 1 into both ears.

As explained above, a stimulus is given to the vagus nerve 10a and the glossopharyngeal nerve 10b which exist in the drum membrane 10 by inserting the appetite adjusting tool 1 into the external auditory canal 9, and this stimulus has an effect of restricting appetite. Therefore, it becomes possible to reduce the volume of a meal, or restrict calories without too much effort, and this enables one to achieve an effective dieting.

The above-described appetite restricting effect varies depending on individuals and various conditions such as the difference in sex, difference in weight, difference in age, personal characteristics, etc. However, as a standard, about 1 minute to 5 minutes are desirable for each insertion of the appetite adjusting tool 1. Further, it is sufficient that the appetite adjusting tool 1 should be used about 2 times a week, since the effect of the appetite adjusting tool 1 can be expected to last for about 2 to 3 days.

Next, the second embodiment of the appetite adjusting tool according to the present invention will be explained with reference to FIGS. 7 and 8.

Figure 7:
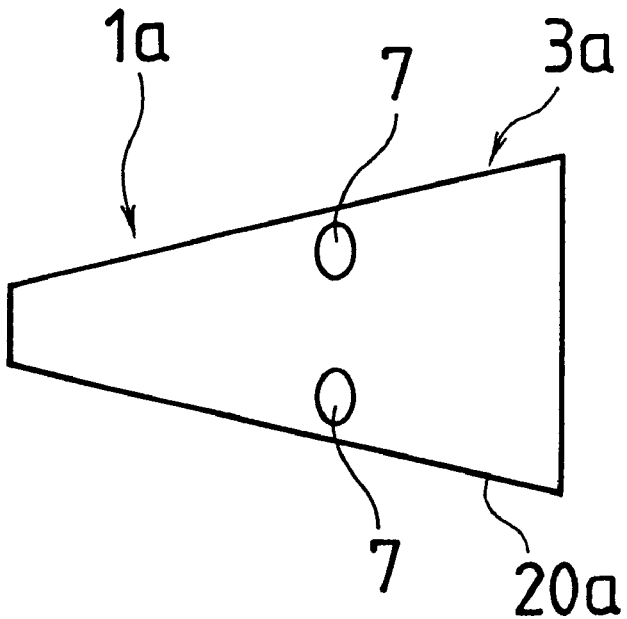
FIG. 7 is a front view of an appetite adjusting tool as a second embodiment of the present invention.
Figure 8:
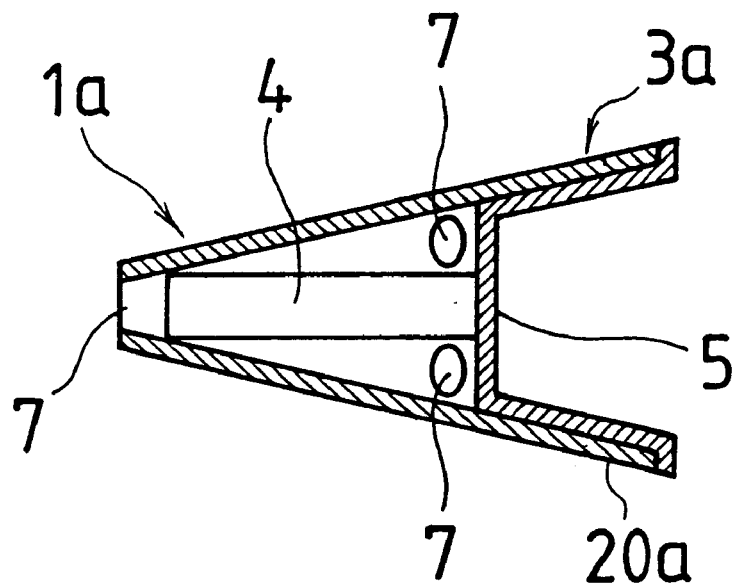
FIG. 8 is a cross sectional view of the appetite adjusting tool shown in FIG. 7.

An appetite adjusting tool 1a according to the second embodiment is composed only of a stimulus giving section 3a having a conical shape with its top truncated, as shown in FIG. 7, and this stimulus giving section 3a is not connected with the bar section 2 as in the case of the appetite adjusting tool 1 according to the first embodiment. This appetite adjusting tool 1a is inserted into the external auditory canal of a person from the side of a vertex of the circular cone. Therefore, hereinafter, the end portion on the side of the vertex of the circular cone will be called a front section and the other end portion will be called a rear section.

The stimulus giving section 3a is composed of a circular cone 20a, a lid 5 for closing one portion of the rear section of the circular cone 20a, and a magnet 4 fixedly arranged in a space formed by the front section of the circular cone 20a and the lid 5. The lid 5 has a cup shape with a wide opening that can be fit into the rear section of the circular cone 20a, as shown by a cross sectional view in FIG. 8. The magnet 4 used in the second embodiment may be a lamination of a plurality of the disk-shaped magnets 4a as shown in FIG. 5A, like the magnet 4 used in the first embodiment, or may be a single bar-shaped magnet 4b as shown in FIG. 6A. The poles of the magnet 4 may be arranged such that S pole is at the end portion of the magnet disposed at the front section of the circular cone 20*a* and N pole is at the end portion of the magnet which is in contact with the lid 5, or vice versa.

When two sets of the appetite adjusting tool 1*a* are used for both ears, one of the appetite adjusting tools 1*a* has its N pole of the magnet 4 disposed on the side of the front section of the circular cone 20*a* and the other appetite adjusting tool 1*a* has its S pole of the magnet 4 disposed on the side of the front section of the circular cone 20*a*.

A plurality of small holes 7 are provided on the side surface of the circular cone 20*a* at a position in front of the lid 5, as shown in FIG. 7. Further, one small hole 7 is provided at the front end of the circular cone 20*a* as shown in FIG. 8. As a result, magnetic lines of force generated from the magnet 4 fixedly arranged in the space formed by the front section of the circular cone 20*a* and the lid 5 can be sent out through these small holes 7.

The method of use and the effect of the appetite adjusting tool 1*a* according to the second embodiment are not particularly different from the method of use and the effect of the appetite adjusting tool 1 according to the first embodiment, and, therefore, explanations thereof will be omitted.

Although the stimulus giving section 3 (or 3*a*) is composed of the hollow section 20 (or 20*a*) and the magnet 4 installed therein in the above-described first and second embodiment, the whole of the stimulus giving section 3 (or 3*a*) may also be formed from a magnet.

What is claimed is:

1. An appetite adjusting tool comprising:
   a stimulus imparting section which has a cross section adapted to be inserted into the external auditory canal of the ear of a person, and having a magnetic unit that provides a magnetic stimulus to nerves which imparts an influence to the sense of taste and appetite from a predetermined position of an internal wall of the external auditory canal.

2. An appetite adjusting tool according to claim 1, wherein
   a cross section of said stimulus imparting section is of a circular shape and a maximum value of the diameter of said circular shape that ranges from about 5 mm to 15 mm.

3. An appetite adjusting tool according to claim 1, wherein
   said stimulus imparting section is composed of a non-magnetic hollow unit, and a thin and long magnet which extends inside said hollow unit along a direction of insertion within the external auditory canal and fixed to said hollow unit.

4. An appetite adjusting tool according to claim 3, wherein said magnet has an N pole at its front end along a direction of insertion of said appetite adjusting tool into the external auditory canal and an S pole at the rear end.

5. An appetite adjusting tool according to claim 3, wherein said magnet has an S pole at its front end along a direction of insertion of said appetite adjusting tool into the external auditory canal and an N pole at the rear end.

6. An appetite adjusting tool according to claim 1, wherein said magnet is formed of one thin and long bar-shaped unit.

7. An appetite adjusting tool according to claim 3, wherein said magnet is formed of a plurality of laminated disk-shaped magnets.

8. An appetite adjusting tool according to claim 1, wherein the magnetic force of said magnet is not lower than 1,000 gausses and not higher than 2,000 gausses.

9. An appetite adjusting tool according to claim 3, wherein said hollow unit has a spherical or spheroidal shape.

10. An appetite adjusting tool according to claim 3, wherein said hollow unit is formed of one of a crystal, a metal, a porcelain and a synthetic resin.

11. An appetite adjusting tool according to claim 3, wherein said hollow unit is formed of cotton.

12. An appetite adjusting tool according to claim 1, wherein said hollow unit has substantially a shape of a circular cone.

13. An appetite adjusting tool according to claim 3, wherein said hollow unit is formed with a plurality of small holes.

14. An appetite adjusting tool according to claim 1, wherein a rear end of said stimulus imparting section, disposed in the direction of its insertion into the external auditory canal, is connected to a bar member of a predetermined length extending along said direction of insertion.

15. An appetite adjusting tool according to claim 14, wherein said bar member is made of a material the same as that of said hollow unit and is integrally formed with said hollow unit.

16. An appetite adjusting tool according to claim 14, wherein a through hole for inserting a chain for a pendant is formed at the rear end portion of said bar member.

17. An appetite adjusting tool according to claim 14, wherein the length of said bar member is about 30 mm.

18. A pair of appetite adjusting tools, each comprising:
   a stimulus imparting section having a cross section adapted for insertion into the external auditory canal of the ear of a person and for providing a magnetic stimulus to nerves for influencing the sense of taste and appetite from a predetermined position of an internal wall of the external auditory canal, wherein
   said stimulus imparting section of each of said appetite adjusting tools is composed of a non-magnetic hollow unit and a magnet fixedly arranged within said hollow unit,
   said magnet in said stimulus imparting source of one of said appetite adjusting tolls has an N pole at a front end along a direction of insertion of said appetite adjusting tool into the external auditory canal, with an S pole disposed at a rear end, and
   said magnet of said stimulus imparting source of the other appetite adjusting tool has an S pole at a front end along a direction of insertion of said appetite adjusting tool into the external auditory canal, with an N pole disposed at a rear end.

* * * * *